United States Patent
Barros Aguirre et al.

(10) Patent No.: US 11,253,500 B2
(45) Date of Patent: Feb. 22, 2022

(54) SANFETRINEM OR A SALT OR ESTER THEREOF FOR USE IN TREATING MYCOBACTERIAL INFECTION

(71) Applicant: GlaxoSmithKline Intellectual Property Development Limited, Brentford (GB)

(72) Inventors: David Barros Aguirre, Madrid (ES); Robert H. Bates, Madrid (ES); Ruben Gonzalez Del Rio, Madrid (ES); Alfonso Mendoza Losana, Madrid (ES); Santiago Ramón García, Saragossa (ES)

(73) Assignee: GLAXOSMITHKLINE INTELLECTUAL PROPERTY DEVELOPMENT LIMITED, Brentford (GB)

(*) Notice: Subject to any disclaimer, the term of this patent is extended or adjusted under 35 U.S.C. 154(b) by 0 days.

(21) Appl. No.: 16/611,908

(22) PCT Filed: May 4, 2018

(86) PCT No.: PCT/EP2018/061615
§ 371 (c)(1),
(2) Date: Nov. 8, 2019

(87) PCT Pub. No.: WO2018/206466
PCT Pub. Date: Nov. 15, 2018

(65) Prior Publication Data
US 2020/0289462 A1 Sep. 17, 2020

(30) Foreign Application Priority Data
May 8, 2017 (EP) .................. 17382255

(51) Int. Cl.
*A61K 31/407* (2006.01)
*A61P 31/06* (2006.01)
*A61K 31/424* (2006.01)
*A61K 31/43* (2006.01)
*A61K 45/06* (2006.01)

(52) U.S. Cl.
CPC .......... *A61K 31/407* (2013.01); *A61K 31/424* (2013.01); *A61K 31/43* (2013.01); *A61K 45/06* (2013.01); *A61P 31/06* (2018.01)

(58) Field of Classification Search
CPC .................................................. A61K 31/407
USPC ....................................................... 514/210
See application file for complete search history.

(56) References Cited

FOREIGN PATENT DOCUMENTS

| EP | 2 085 084 A1 | 8/2009 |
|---|---|---|
| EP | 2 135 871 A1 | 12/2009 |
| RU | 2043354 C1 | 9/1995 |
| WO | WO 92/03437 A1 | 3/1992 |
| WO | WO 1994/021637 A1 | 9/1994 |
| WO | WO 2016/046845 A1 | 3/2016 |
| WO | WO 2016/128949 A1 | 8/2016 |

OTHER PUBLICATIONS

Braggio, et al., *European Journal of Pharmaceutical Sciences*, AL: Evaluation of the role of intestinal and liver metabolism in the conversion of two different ester prodrugs of sanfetrinem to the parent drug in vitro and in vivo using different rat tissues and a surgically prepared rat mode, 16(12):45-51 (2002).
Bush, et al., *Expert Opinion on Therapeutic Pate, Informa Healthcare*, New b-lactam antibiotics and b-lactamase inhibitors, 20(10):1277= 1293 (2010).
Shinobu, et al., *Antimicrobial Agents and Chemotherapy, American Society for Microbiology*, In vivo antibacterial activities of sanfetrinem cilexetil, a new oral tricyclic antibiotic, 42(7)_:1858-1861 (1998).
Wivagg, et al., *The Journal of Antibiotics*, Mechanisms of [beta]-lactam killing and resistance in the context of *Mycobacterium tuberculosis*, 67(9):645-654 (2014).
Kurz, et al. "Reappraising the use of β-lactams to treat tuberculosis". Expert Review of Anti-Infective Therapy, 10(9): 999-1006 (2012).
Dincer, et al. "The Vitro Efficacy of β-Lactam and β-Lactamase Inhibitors Against Multidrug Resistant Clinical Strains of *Mycobacterium tuberculosis*". International Journal of Antimicrobial Agents, 23: 408-411 (2004).
Andreas H. Diacon. "β-Lactams against Tuberculosis—New Trick for an Old Dog?" New England Journal of Medicine, 375(4): 392-393 (Jul. 28, 2016).
Rullas, et al. "Combinations of β-Lactam Antibiotics Currently in Clinical Trials are Efficacious in a DHP-I-Deficient Mouse Model of Tuberculosis Infection". Antimicrobial Agents and Chemotherapy, 59(8): 4997-4999 (Aug. 1, 2015).

(Continued)

*Primary Examiner* — Taofiq A Solola
(74) *Attorney, Agent, or Firm* — Robert H. Brink; Scott Young; Duke M. Fitch

(57) ABSTRACT

The present invention relates to

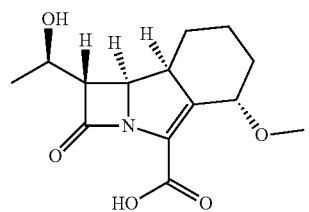

or a pharmaceutically acceptable salt or ester prodrug thereof for use in the treatment of a mycobacterial infection or disease resulting from a mycobacterial infection, such as tuberculosis.

14 Claims, 8 Drawing Sheets

(56) References Cited

OTHER PUBLICATIONS

Pagliotto, et al. "Anti *Mycobacterium tuberculosis* Activity of Antituberculosis Drugs and Amoxicillin/Clavulanate Combination". Journal of Microbiology, Immunology and Infection, 49: 980-983 (2016).
Gonzalo, et al. Is There a Place for β-Lactams in the Treatment of Multidrug-Resistant/Extensively Drug-Resistant Tuberculosis? Synergy Between Meropenem and Amoxicillin/Clavulanate. Journal of Antimicrobial Chemotherapy, 68: 366-369 (2013).
Lowther, et al. "P706: Synergistic, Additive or Indifferent Effects of Sanfetrinem, a New Oral Trinem, in Combination with Other Antimicrobial Agents". Clinical Microbiology and Infection, 3(Supp. 2): 169 (Jul. 1, 1995).
Dhar, et al. "Rapid Cytolysis of *Mycobacterium tuberculosis* by Faropenem, an Orally Bioavailable β-Lactam Antibiotic". Antimicrobial Agents and Chemotherapy, 59(2): 1308-1319 (Feb. 27, 2015).

SANFETRINEM OR A SALT OR ESTER THEREOF FOR USE IN TREATING MYCOBACTERIAL INFECTION

The work leading to this invention has received funding from the People Programme (Marie Curie Actions) of the European Union's Seventh Framework Programme (FP7/2007-2013) under REA grant agreement no. 291799.

FIELD OF THE INVENTION

The present invention relates to sanfetrinem, or a pharmaceutically acceptable salt or ester prodrug thereof, and its use in the treatment of a mycobacterial infection or a disease resulting from a mycobacterial infection. More specifically, the present invention relates to the use of sanfetrinem, or a pharmaceutically acceptable salt or ester prodrug thereof, in the treatment of tuberculosis. In particular, the present invention relates to the prodrug, sanfetrinem cilexetil, and its use in the treatment of tuberculosis.

BACKGROUND TO THE INVENTION

Nearly ten million people are infected with tuberculosis (TB) each year, causing 1.5 million deaths each year, according to a report published by The World Health Organisation in 2014. Despite available treatments for tuberculosis, the global disease burden remains a major problem owing to *Mycobacterium tuberculosis*, the causative bacterial agent for TB, becoming resistant to many of the treatments.

Although TB is caused by bacterial infection, the use of the most prominent class of antibiotics, the β-lactams, has been largely ignored. Despite the fact that the dozens of approved β-lactam drugs make up an estimated two thirds of the global antibiotic market, their evaluation against TB was limited by early failures in clinical trials and assumptions that the lypophilic mycobacterial cell wall was impermeable to such highly polar molecules.

Sanfetrinem cilexetil is an experimental antibiotic from the 1990s linked with infections caused by a variety of bacterial species but not including mycobacteria.

Owing to the ever-growing emergence of multi-drug resistant strains of *Mycobacterium tuberculosis* and continued high incidence of TB, there exists an urgent need to provide further drug compounds for the treatment of TB.

SUMMARY OF THE INVENTION

In a first aspect of the present invention, there is provided

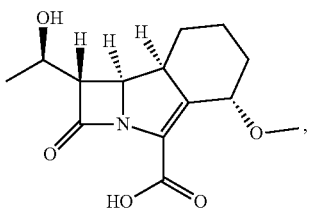 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof for use in the treatment of a disease resulting from a mycobacterial infection.

In a second aspect of the present invention, there is provided

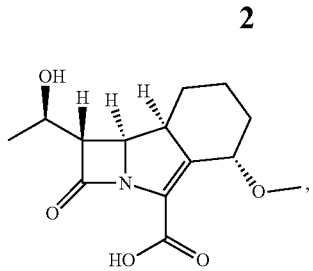

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof for use in the treatment of a mycobacterial infection.

In a third aspect of the present invention, there is provided

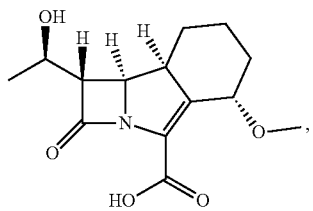 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof for use in the treatment of tuberculosis.

In a fourth aspect of the present invention, there is provided a method for the treatment of a disease resulting from a mycobacterial infection in a patient in need thereof, comprising administering to said patient a therapeutically effective amount of

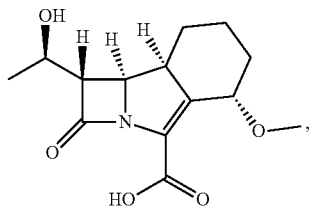 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof.

In a fifth aspect of the present invention, there is provided a method for the treatment of a mycobacterial infection in a patient in need thereof, comprising administering to said patient a therapeutically effective amount of

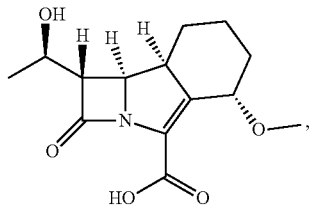 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof.

In a sixth aspect of the present invention, there is provided a method for the treatment of tuberculosis in a patient in need thereof, comprising administering a therapeutically effective amount of

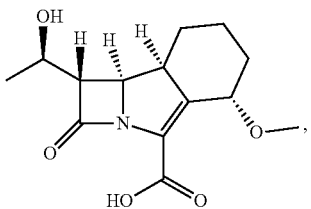 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof.

In a seventh aspect of the present invention, there is provided use of

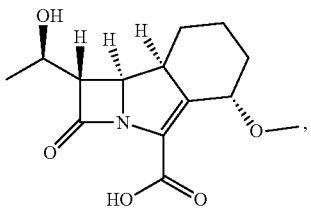 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof in the manufacture of a medicament for use in the treatment of tuberculosis, a mycobacterial infection or a disease resulting from a mycobacterial infection.

In an eighth aspect of the present invention, there is provided a pharmaceutical composition comprising (a)

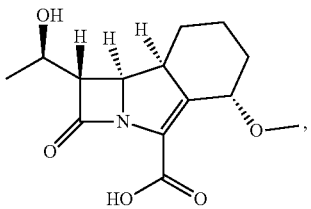 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof; and (b) a pharmaceutically acceptable excipient, for use in the treatment of tuberculosis, a mycobacterial infection or a disease resulting from a mycobacterial infection.

In a ninth aspect of the present invention, there is provided a combination of (a)

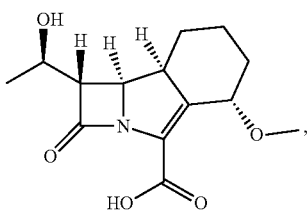 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof; and (b) a further other anti-tuberculosis agent, for use in the treatment of a mycobacterial infection, a disease resulting from a mycobacterial infection, or tuberculosis.

In a tenth aspect of the present invention, there is provided a combination of (a)

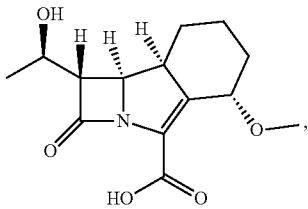 [SMILES: CO[C@H]1CCC[C@H]2C1=C(C(=O)O)N1C(=O)[C@H]([C@@H](C)O)[C@@H]21]

having the name (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid, or a pharmaceutically acceptable salt or ester prodrug thereof; and (b) a β-lactamase inhibitor.

DETAILED DESCRIPTION OF THE INVENTION

Figure 1:
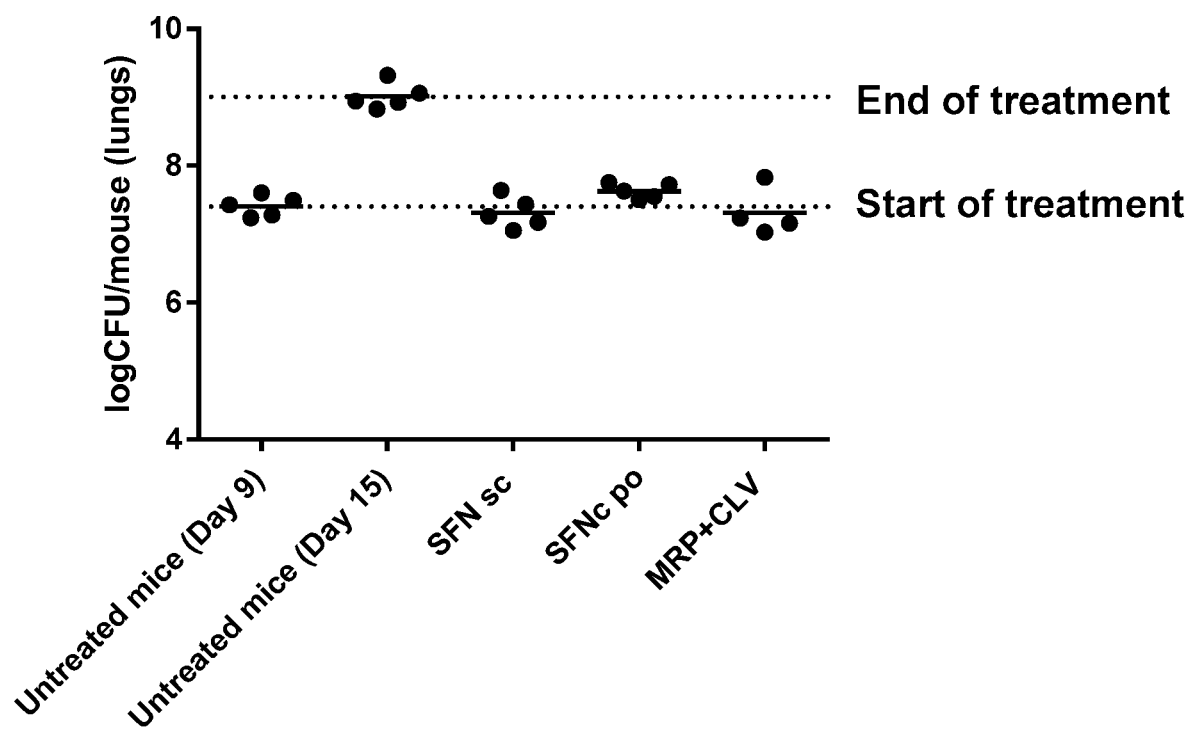
FIG. 1 illustrates the results of a mouse model used to evaluate in vivo anti-tubercular activity of sanfetrinem and sanfetrinem cilexetil.

The present invention relates to a compound having the following structure (hereinafter also referred to as compound A):

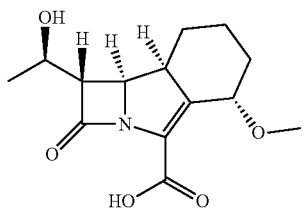 [SMILES: CO[C@H]1CCC[C@H]2C1=C(C(=O)O)N1C(=O)[C@H]([C@@H](C)O)[C@@H]21]

or a pharmaceutically acceptable salt or ester prodrug thereof for use in the treatment of a disease resulting from a mycobacterial infection. A mycobacterial infection is one caused by infection with a *Mycobacterium*.

The name of compound A is (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid.

The *Mycobacterium* may be a member of one of the following groups of *Mycobacterium*: *Mycobacterium tuberculosis* complex (MTC), *Mycobacterium avium* complex (MAC), *Mycobacterium gordonae* clade, *Mycobacterium kansasii* clade, *Mycobacterium chelonae* clade, *Mycobacterium fortuitum* clade, *Mycobacterium parafortuitum* clade or *Mycobacterium vaccae* clade. The *Mycobacterium* may also be *Mycobacterium ulcerans* or *Mycobacterium leprae*.

Members of *Mycobacterium tuberculosis* complex (MTC) include *Mycobacterium* tuberculosis, *Mycobacterium* africanum, *Mycobacterium* bovis, *Mycobacterium bovis* BCG, *Mycobacterium* canetti, *Mycobacterium* caprae, *Mycobacterium* microti and *Mycobacterium* pinnipedii. These mycobacteria are causative agents of human and animal tuberculosis. *Mycobacterium tuberculosis* is the major cause of human tuberculosis.

In one embodiment, the infection is one caused by infection with a *Mycobacterium* which is a member of *Mycobacterium tuberculosis* complex (MTC).

In one embodiment, the infection is a *Mycobacterium tuberculosis* infection. In other words, the mycobacterial infection is caused by infection with *Mycobacterium* tuberculosis.

Members of *Mycobacterium avium* complex (MAC) include *Mycobacterium* avium, *Mycobacterium avium* paratuberculosis, *Mycobacterium* avium silaticum, *Mycobacterium* avium hominissuis, *Mycobacterium* columbiense and *Mycobacterium* indicus pranii.

Members of *Mycobacterium gordonae* clade include *Mycobacterium* asiaticum and *Mycobacterium* gordonae.

Members of *Mycobacterium kansasii* clade include *Mycobacterium* gastri and *Mycobacterium* kansasii.

Members of *Mycobacterium chelonae* clade include *Mycobacterium* abscessus, *Mycobacterium* bolletii and *Mycobacterium* chelonae.

Members of *Mycobacterium fortuitum* clade include *Mycobacterium* boenickei, *Mycobacterium* brisbanense, *Mycobacterium* cosmeticum, *Mycobacterium* fortuitum, *Mycobacterium fortuitum* subspecies *acetamidolyticum*, *Mycobacterium* houstonense, *Mycobacterium* mageritense, *Mycobacterium* neworleansense, *Mycobacterium* peregrinum, *Mycobacterium* porcinum, *Mycobacterium* senegalense and *Mycobacterium* septicum.

Members of *Mycobacterium parafortuituum* clade include *Mycobacterium* austroafricanum, *Mycobacterium* diemhoferi, *Mycobacterium* frederiksbergense, *Mycobacterium* hodleri, *Mycobacterium* neoaurum and *Mycobacterium* parafortuitum.

Therefore, the mycobacterial infection may be caused by infection with a *Mycobacterium* selected from the following: *Mycobacterium* tuberculosis, *Mycobacterium* africanum, *Mycobacterium* bovis, *Mycobacterium bovis* BCG, *Mycobacterium* canetti, *Mycobacterium* caprae, *Mycobacterium* microti, *Mycobacterium* pinnipedii, *Mycobacterium* avium, *Mycobacterium* avium paratuberculosis, *Mycobacterium* avium silaticum, *Mycobacterium* avium hominissuis, *Mycobacterium* columbiense, *Mycobacterium* indicus pranii, *Mycobacterium* asiaticum, *Mycobacterium* gordonae, *Mycobacterium* gastri, *Mycobacterium* kansasii, *Mycobacterium* abscessus, *Mycobacterium* bolletii, *Mycobacterium* chelonae, include *Mycobacterium* boenickei, *Mycobacterium* brisbanense, *Mycobacterium* cosmeticum, *Mycobacterium* fortuitum, *Mycobacterium fortuitum* subspecies *acetamidolyticum*, *Mycobacterium* houstonense, *Mycobacterium* mageritense, *Mycobacterium* neworleansense, *Mycobacterium* peregrinum, *Mycobacterium* porcinum, *Mycobacterium* senegalense, *Mycobacterium* septicum, *Mycobacterium* austroafricanum, *Mycobacterium* diemhoferi, *Mycobacterium* frederiksbergense, *Mycobacterium* hodleri, *Mycobacterium* neoaurum, *Mycobacterium* parafortuitum, *Mycobacterium* ulcerans and *Mycobacterium* leprae.

Diseases caused by infection with a *Mycobacterium* include, but are not limited to, tuberculosis (e.g. from *Mycobacterium tuberculosis*), leprosy (e.g. from *Mycobacterium leprae*), Johne's disease (e.g. from *Mycobacterium avium* subspecies paratuberculosis), Buruli or Bairnsdale ulcer (e.g. from *Mycobacterium ulceran*), Crohn's disease (e.g. from *Mycobacterium avium* subspecies paratuberculosis), cystic fibrosis (e.g. from non-tuberculosis mycobacteria such as *Mycobacterium avium-intracellulare* complex and *Mycobacterium abscessus*) pulmonary disease or pulmonary infection, pneumonia, bursa, synovial, tendon sheaths, localized abscess, lymphadenitis, skin and soft tissue infections, Lady Windermere syndrome (e.g. from *Mycobacterium avium* complex (MAC)), MAC lung disease, disseminated *Mycobacterium avium* complex (DMAC), disseminated *Mycobacterium avium intraceullulare* complex (DMAIC), hot-tub lung (e.g. from *Mycobacterium avium* complex), MAC mastitis, MAC pyomyositis, or granuloma disease.

In an embodiment, the disease resulting from a mycobacterial infection is tuberculosis, such that the present invention relates to compound A, or a pharmaceutically acceptable salt or ester prodrug thereof, for use in the treatment of tuberculosis.

The invention also relates to compound A, or a pharmaceutically acceptable salt or ester prodrug thereof, for use in the treatment of a mycobacterial infection. In a particular embodiment, the mycobacterial infection is a *Mycobacterium tuberculosis* infection.

More specifically, the invention relates to compound A, or a pharmaceutically acceptable salt or ester prodrug thereof, for use in the treatment of tuberculosis. In an embodiment, the treatment of tuberculosis may be directed to the treatment of multidrug-resistant tuberculosis, extensively drug-resistant, or drug-sensitive tuberculosis.

In one embodiment, the treatment of tuberculosis is directed to multidrug-resistant or extensively drug-resistant tuberculosis.

In addition, the treatment may be directed to pulmonary and/or extra-pulmonary tuberculosis. The treatment may also be directed to the treatment of latent TB.

Compound A is also known as sanfetrinem or GV104326. A sodium salt of sanfetrinem would be known as sanfetrinem sodium. A potassium salt of sanfetrinem would be known as sanfetrinem potassium, and so on.

More particularly, the invention relates to an ester prodrug of compound A for use in the treatment of a mycobacterial infection or disease resulting from a mycobacterial infection, wherein the prodrug has the following structure

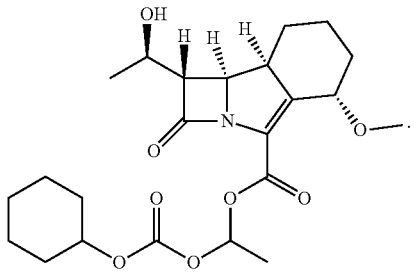 [SMILES: CO[C@H]1CCC[C@H]2C1=C(C(=O)OC(C)OC(=O)OC1CCCCC1)N1C(=O)[C@H]([C@@H](C)O)[C@@H]21]

This ester prodrug has the name (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate. This prodrug is also known as sanfetrinem cilexetil or GV118819X.

Thus, the invention also relates to (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate, i.e.

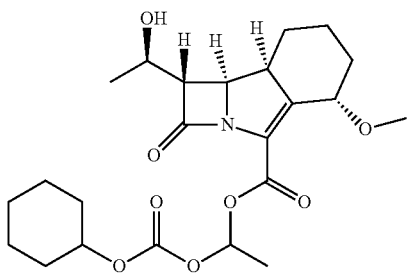 [SMILES: CO[C@H]1CCC[C@H]2C1=C(C(=O)OC(C)OC(=O)OC1CCCCC1)N1C(=O)[C@H]([C@@H](C)O)[C@@H]21]

for use in the treatment of tuberculosis.

It will be appreciated that the ester prodrug (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate (depicted above) is a mixture of diastereoisomers, also known as epimers. The diastereoisomers may be present in the mixture in equal amounts (a 1:1 mixture) or in unequal amounts. Alternatively, the compound may be present as one diastereoisomer. Each diastereoisomer is depicted below.

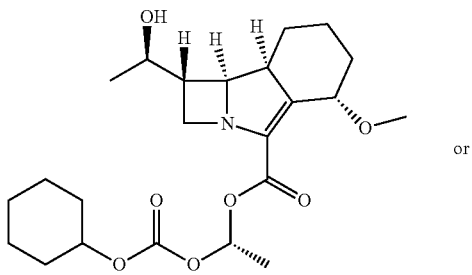

or

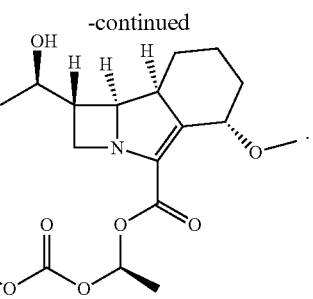

Such single diastereoisomers may be obtained by separation of a mixture of diastereoisomers.

The prodrug described above may be advantageously used in the treatment of tuberculosis because it can be administered to patients orally.

An alternative prodrug is (1S,5S,8aS,8bR)-(S)-1-((ethoxycarbonyl)oxy)ethyl 1-((R)-1-hydroxyethyl)-5-methoxy-2-oxo-1,2,5,6,7,8,8a,8b-octahydroazeto[2,1-a]isoindole-4-carboxylate, having the following structure,

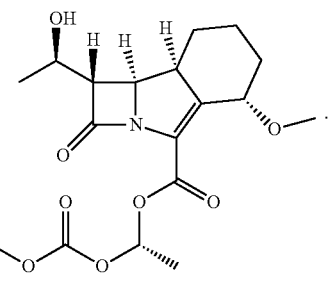

This prodrug may be prepared according to the procedures described in, for example, WO 94/21637 or similar methods.

All chemical structures have been named using ChemBioDraw Ultra version 12.0 (by conversion of structure to name).

It is to be understood that references herein to compound A or a salt thereof includes compound A as a free acid, or as a pharmaceutically acceptable salt thereof. Thus, in one embodiment, the invention is directed to compound A. In another embodiment, the invention is directed to a pharmaceutically acceptable salt of compound A. In another embodiment, the invention is directed to an ester prodrug of compound A.

The term "ester prodrug" refers to compound A wherein an ester has been formed on/using the free carboxylic acid moiety that is present. In other words, "ester prodrug" means an ester has been formed using the free acid available in the structure below.

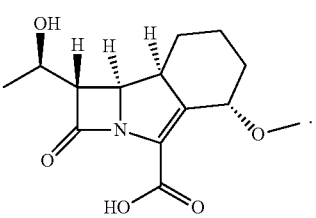 [SMILES: CO[C@H]1CCC[C@H]2C1=C(C(=O)O)N1C(=O)[C@H]([C@@H](C)O)[C@@H]21]

As example of such an ester prodrug is a compound having the following structure

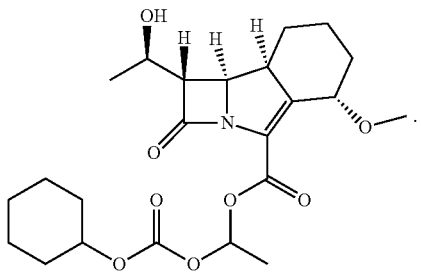 [SMILES: CO[C@H]1CCC[C@H]2C1=C(C(=O)OC(C)OC(=O)OC1CCCCC1)N1C(=O)[C@H]([C@@H](C)O)[C@@H]21]

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, *J. Pharm. Sci.*, 1977, 66, 1-19, or those listed in P H Stahl and C G Wermuth, editors, *Handbook of Pharmaceutical Salts; Properties, Selection and Use, Second Edition* Stahl/Wermuth: Wiley—VCH/ VHCA, 2011 (see http://www.wiley.com/WileyCDA/Wiley-Title/productCd-3906390519.html).

Suitable pharmaceutically acceptable salts can include base addition salts.

Such base addition salts can be formed by reaction of (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid with the appropriate base, optionally in a suitable solvent such as an organic solvent, to give the salt which can be isolated by a variety of methods, including crystallisation and filtration.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

Particular pharmaceutically acceptable salts according to the present invention are the sodium salt and potassium salt of compound A, such that the compound to be administered to a patient for treatment is potassium (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylate or sodium (1 S,5S,8aS,8bR)-1-((R)-1-hydroxyethyl)-5-methoxy-2-oxo-1, 2,5,6,7,8,8a,8b-octahydroazeto[2,1-a]isoindole-4-carboxylate, depicted as follows

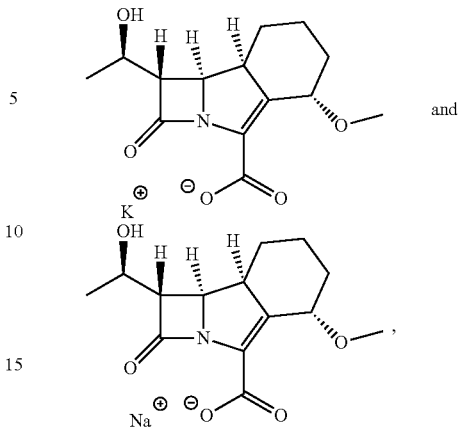

respectively.

In one embodiment, the pharmaceutically acceptable salt of compound A is the sodium salt.

It will be appreciated that the compound (1S,5S,8aS, 8bR)-1-((R)-1-hydroxyethyl)-5-methoxy-2-oxo-1,2,5,6,7,8, 8a,8b-octahydroazeto[2,1-a]isoindole-4-carboxylic acid or a pharmaceutically acceptable salt thereof, or its prodrug, (1 S,5S,8aS,8bR)-1-(((cyclohexyloxy)carbonyl)oxy)ethyl 1-((R)-1-hydroxyethyl)-5-methoxy-2-oxo-1,2,5,6,7,8,8a, 8b-octahydroazeto[2,1-a]isoindole-4-carboxylate could be in any suitable solvated (e.g. hydrated) and/or polymorphic forms thereof.

The compound (1 S,5S,8aS,8bR)-1-((R)-1-hydroxyethyl)-5-methoxy-2-oxo-1,2,5,6,7,8,8a,8b-octahydroazeto [2,1-a]isoindole-4-carboxylic acid or a pharmaceutically acceptable salt thereof, or its prodrug, (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto [2,1-a]isoindole-4-carboxylate may be prepared according to the procedures described in EP0416953 and WO 94/21637 or similar methods.

Specifically, (1 S,5S,8aS,8bR)-1-((R)-1-hydroxyethyl)-5-methoxy-2-oxo-1,2,5,6,7,8,8a,8b-octahydroazeto[2,1-a] isoindole-4-carboxylic acid or its salt thereof may be prepared according to the procedures described in Examples 4 and 5 of WO 94/21637.

Specifically, the prodrug, (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a] isoindole-4-carboxylate may be prepared according to the procedure described in Example 1 of WO 92/03437. Other ester prodrugs may be prepared according to similar methods and methods known to those skilled in the art.

In a further aspect of the invention, there is provided a method for the treatment of a disease resulting from a mycobacterial infection in a patient in need thereof, comprising administering to said patient a therapeutically effective amount of (1S,5S,8aS,8bR)-1-((R)-1-hydroxyethyl)-5-methoxy-2-oxo-1,2,5,6,7,8,8a,8b-octahydroazeto[2,1-a] isoindole-4-carboxylic acid or a pharmaceutically acceptable salt or ester prodrug thereof.

The mycobacterial infection may be caused by one of the mycobacteria selected from the list hereinbefore described, such as *Mycobacterium* tuberculosis.

In an embodiment, the disease to be treated is tuberculosis. Therefore, in an embodiment, the invention also relates to a method of treatment of tuberculosis in a patient in need thereof, comprising administering to said patient a therapeutically effective amount of (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof.

In a further aspect, there is provided a method for the treatment of a mycobacterial infection in a patient in need thereof, comprising administering to said patient a therapeutically effective amount of (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof.

The mycobacterial infection may be caused by one of the mycobacteria selected from the list described above. In an embodiment, the mycobacterial infection is a *Mycobacterium tuberculosis* infection, such that the invention relates to a method of treatment of a *Mycobacterium tuberculosis* infection.

In a further aspect, there is provided a method for the treatment of tuberculosis in a patient in need thereof, comprising administering to said patient a therapeutically effective amount of (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof.

In one embodiment, there is provided a method for the treatment of tuberculosis in a patient in need thereof, which comprises administering to said patient a therapeutically effective amount of an ester prodrug of compound A. In particular, the ester prodrug is (1 S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate, having the structure depicted above.

In another embodiment, there is provided a method for the treatment of tuberculosis in a patient in need thereof, comprising administering to said patient a therapeutically effective amount of a pharmaceutically acceptable salt of compound A. In particular, the pharmaceutically acceptable salt is the sodium salt, such that the agent administered to a patient is sodium (1S,5S,8aS,8bR)-1-((R)-1-hydroxyethyl)-5-methoxy-2-oxo-1,2,5,6,7,8,8a, 8b-octahydroazeto[2,1-a]isoindole-4-carboxylate.

In one embodiment, the patient in need thereof is a human patient. The term patient is intended to refer to a person suffering from, or infected with, a mycobacterial infection, a disease resulting from a mycobacterial infection or tuberculosis.

Further provided is use of the compound (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof in the manufacture of a medicament for use in the treatment of a disease resulting from a mycobacterial infection, or in the treatment of a mycobacterial infection. In particular, the invention relates to use of the compound (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof in the manufacture of a medicament for use in the treatment of tuberculosis.

In particular, also provided is the use of sodium (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylate or (1 S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate in the manufacture of a medicament for use in the treatment of tuberculosis.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

It will be appreciated by those skilled in the art that references herein to treatment refer to the treatment of established conditions, including e.g., a mycobacterial infection, a disease resulting from a mycobacterial infection and/or tuberculosis. However, (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid as well as pharmaceutically acceptable salts or ester prodrugs thereof may, depending on the condition, also be useful in the prevention of a mycobacterial infection, a disease resulting from a mycobacterial infection and/or tuberculosis. Thus, in one embodiment, there is provided the treatment or prevention of a disease. In another embodiment, there is provided the treatment of a disease. In a further embodiment, there is provided the prevention of a disease.

While is it possible that, for use in the treatment of a mycobacterial infection, a disease resulting from a mycobacterial infection or tuberculosis, (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid as well as pharmaceutically acceptable salts or ester prodrugs thereof, may be administered alone, it is common to present the active ingredient as a pharmaceutical composition comprising one or more pharmaceutically acceptable excipient(s).

Therefore, in one embodiment, there is also provided a pharmaceutical composition comprising (a) sodium (1 S,5S,8aS,8bR)-1-((R)-1-hydroxyethyl)-5-methoxy-2-oxo-1,2,5,6,7,8,8a, 8b-octahydroazeto[2,1-a]isoindole-4-carboxylate or the prodrug, (1 S,5 S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate, and (b) a pharmaceutically acceptable excipient, for use in the treatment of a mycobacterial infection, a disease resulting from a mycobacterial infection or tuberculosis.

Pharmaceutical compositions may be administered by any appropriate route, for example by the oral (including buccal or sublingual), inhaled, intranasal, topical (including buccal, sublingual or transdermal) or parenteral (including subcutaneous, intramuscular, intravenous or intradermal) route.

In one embodiment the pharmaceutical composition is administered by oral route of administration. When the pharmaceutical composition is for oral administration, in particular, the ester prodrug (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate is used as the active pharmaceutical ingredient.

In one embodiment the pharmaceutical composition is administered by intravenous route of administration. When the pharmaceutical composition is for intravenous administration, in particular the sodium or potassium salt of compound A is used as the active pharmaceutical ingredient.

Suitable pharmaceutically acceptable excipients include the following types of excipients: carriers, diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants and buffering agents.

Suitable methods for formulating (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof include those that are familiar to those skilled in the art, which are described in Remington: The Science and Practice of Pharmacy, 21$^{st}$ Edition 2006.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

For administration of the active ingredient, e.g. the ester prodrug, (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate), the dosage may be from 100 mg to 2000 mg or 100 mg to 1000 mg. For example, the dosage may be from 250 mg to 500 mg. In particular, the oral dosage may be from 250 mg to 1000 mg administered twice daily, thereby providing a total daily dose of 500 mg to 2000 mg. The oral dosage may be administered once daily. The total amount of active ingredient administered per day may be 500, 1000 or 2000 mg.

For intravenous administration, e.g. (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt thereof, the dose may be up to 1 g three times per day, providing a total daily dose of 3 g. Alternatively, the total daily dose may be 1.5 g or 2 g per day.

The compound may be given in a single dose per day or in a number (such as two, three, four, five or six) of sub-doses per day such that the total daily dose is the same. An effective amount of a pharmaceutically acceptable salt or ester prodrug thereof, may be determined as a proportion of the effective amount of the compound (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt thereof per se.

An example of an oral tablet formulation that may be used is described in EP502465, which is as follows.

|  | mg/tablet |
|---|---|
| Active ingredient e.g. (1S,5S,8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate | 320 |
| Lactose | 150 |
| Ethyl Cellulose | 20 |
| Sodium Lauryl Sulfate | 7 |
| Magnesium Stearate | 3 |
| Tablet Core | 500 mg |

The active ingredient and the lactose may be blended together and then granulated using water as the granulation fluid. The dried granules may then be blended with ethyl cellulose, sodium lauryl sulfate and magnesium stearate and the tablet core formed using an appropriate punch. The tablet may then be coated (e.g. with an enteric coating) using conventional techniques and coatings.

For use in the invention, the compound (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof may be employed alone or in combination with further therapeutic agents. In particular, the compound (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof may be employed in combination with further anti-tuberculosis and/or an antiviral agents, including antiretroviral agents.

For example, also disclosed herein is a combination of (a) compound A or a pharmaceutically acceptable salt or ester prodrug thereof, and (b) a further anti-tuberculosis agent.

Therefore, the present invention also includes a combination of (a) compound A or a pharmaceutically acceptable salt or ester prodrug thereof, and (b) a further anti-tuberculosis agent, for use in the treatment of a mycobacterial infection, a disease resulting from a mycobacterial infection, or tuberculosis. In one embodiment, the combination is for use in the treatment of tuberculosis.

In an embodiment, the combination may comprise two, three, four, five, six or seven additional anti-tuberculosis agents. For example, in the treatment of multidrug-resistant tuberculosis, it is common that combinations of four or more agents are administered to patients. For example, in the treatment of drug-sensitive tuberculosis, it is common that combinations of three or four agents are administered to patients.

The further anti-tuberculosis agent may be an agent in development, approved or recommended for the treatment of tuberculosis.

In one embodiment, the anti-tuberculosis agent may be selected from isoniazid, rifampin, pyrazinamide, ethambutol, moxifloxacin, rifapentine, clofazimine, ethionamide, prothionamide, isoxyl, thiacetazone, rifabutin, a diarylquinoline such as bedaquiline (TMC207) or TBAJ-587, nitroimidazo-oxazine PA-824 (pretomanid), delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656A (also known as GSK070), GSK2556286, GSK3211830, a benzothiazinone such as BTZ043 or PBTZ169, an azaindole such as TBA-7371, a dinitrobenzamide, or a beta-lactam such as meropenem, faropenem, ertapenem, tebipenem or beta-lactam combinations such as AUGMENTIN (amoxicillin-clavulanate).

In one embodiment, the anti-tuberculosis agent may be AUGMENTIN, i.e. amoxicillin-clavulanate. Therefore, also disclosed herein is the combination of Compound A or a pharmaceutically acceptable salt or ester prodrug thereof and AUGMENTIN.

In another embodiment, the anti-tuberculosis agent may be selected from delamanid, rifampicin and ethambutol. Therefore, also disclosed herein is the combination of Compound A or a pharmaceutically acceptable salt or ester prodrug thereof and at least one of delamanid, rifampicin and ethambutol.

A combination for use according to the present invention may further comprise an antiviral agent, including an antiretroviral agents.

Such antiretroviral agents may be selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

A combination may conveniently be presented for use in the form of a pharmaceutical composition or formulation. Therefore, also contemplated herein is a pharmaceutical composition comprising (a) compound A or a pharmaceutically acceptable salt or ester prodrug thereof, as herein described, together with (b) a further other anti-tuberculosis drug and (c) optionally an antiviral agent including antiretroviral agents, and (d) one or more pharmaceutically acceptable excipients.

The compound (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof and the further therapeutically active agent(s) (such as the anti-tuberculosis agent and antiviral agents) may be administered together or separately and, when administered separately, this may occur separately or sequentially in any order (by the same or by different routes of administration).

In one embodiment, compound A or a pharmaceutically acceptable salt or ester prodrug thereof is co-administered with a further anti-tuberculosis agent. By the term "co-administered" is meant either simultaneous administration or any manner of separate administration of compound A or a pharmaceutically acceptable salt or ester prodrug thereof, and a further anti-tuberculosis agent known to be useful in the treatment of a mycobacterial infection, disease resulting from a mycobacterial infection or tuberculosis, particularly tuberculosis.

The amounts of (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof and the further therapeutically active agent(s) and the relative timings of administration will be selected in order to achieve the desired combined therapeutic effect.

The compound (1 S,5S,8aS,8bR)-1-((R)-1-hydroxyethyl)-5-methoxy-2-oxo-1,2,5,6,7,8,8a,8b-octahydroazeto[2,1-a]isoindole-4-carboxylic acid or a pharmaceutically acceptable salt or ester prodrug thereof may be administered in combination with a β-lactamase inhibitor.

Therefore, the invention also relates to a combination of the ester prodrug of sanfetrinem, (1 S, 5S, 8aS,8bR)-1-(((cyclohexyloxy)carbonyl)oxy)ethyl 1-((R)-1-hydroxyethyl)-5-methoxy-2-oxo-1,2,5,6,7,8,8a,8b-octahydroazeto[2,1-a]isoindole-4-carboxylate, and a β-lactamase inhibitor.

The invention further relates to a combination of the sodium salt of sanfetrinem, sodium (1S,5S,8aS,8bR)-1-((R)-1-hydroxyethyl)-5-methoxy-2-oxo-1,2,5,6,7,8,8a,8b-octahydroazeto[2,1-a]isoindole-4-carboxylate, and a β-lactamase inhibitor.

In one embodiment, the β-lactamase inhibitor is selected from clavulanic acid or a water soluble salt thereof (such as potassium clavulanate), tazobactam, avibactam and sulbactam.

In one embodiment, the β-lactamase inhibitor is clavulanic acid or a water-soluble salt thereof, such as potassium clavulanate.

In one embodiment, the β-lactamase inhibitor may be provided as a combination of amoxicillin and potassium clavulanate known as co-amoxiclav (also known as, for example, AUGMENTIN). The co-amoxiclav may be administered as 375 mg or 625 mg tablets, wherein potassium clavulanate is present in an amount equivalent to 125 mg of clavulanic acid. Additionally, co-amoxiclav may be administered as 1000 mg tablets, wherein potassium clavulanate is present in an amount equivalent to 125 mg clavulanic acid. Alternatively, co-amoxiclav may be administered as a total amount per day of 4000 mg of amoxicillin wherein potassium clavulanate is present in an amount equivalent to 250 mg, i.e. administration of 1000 mg tablets wherein potassium clavulanate is present in an amount of 62.5 mg, wherein two tablets are administered twice a day.

The invention will now be described with reference to the following examples.

EXAMPLES

The sodium salt of sanfetrinem was tested in the following extracellular and intracellular viability assays. Some other β-lactam drugs were also tested in the same assay—meropenem, tebipenem, ertapenem and faropenem.

Sanfetrinem was prepared in accordance with one of the methods described in EP0416953 and WO 94/21637 (see for example, Examples 4 and 5). In the assays described below, the sodium salt of sanfetrinem was used.

Faropenem sodium was purchased from AOKChem—CN (Ref A6030).

Meropenem was purchased from Combi Blocks, USA (Ref ST-9229).

Tebipenem was purchased from Chemexpress (Shanghai Haoyuan) Co., Ltd. (Ref HY-A0076).

Ertapenem was purchased from Amatek (Ref DM-0004).

Potassium clavulanate was used as the clavulanic acid source, referred to as "clav" in the Tables below.

Abbreviation List

DMSO: Dimethyl sulfoxide
ADC: Albumin/dextrose/catalase
CFU: colony forming unit
FBS: Foetal Bovine Serum
Mtb: *Mycobacterium* tuberculosis
RPMI: Roswell Park Memorial Institute
PBS: Phosphate buffered saline
MIC Determination The measurement of the Minimum Inhibitory Concentration (MIC) against *M. tuberculosis* H37Rv for each tested compound was performed in 96-well flat-bottom, polystyrene microtiter plates in a final volume of 200 μL.

Ten two-fold drug dilutions of the test compound in neat DMSO starting at 80 μM were performed from column 1 to 10. Moxifloxacin (MX) was used as a dose response compound control with 2-fold dilutions of MX starting at 1 μg/ml in column 11. In G-12 and H-12 Rifampicin was dispensed at 1 μg/ml as a non-growing control. From A12 to F12 DMSO was dispensed as the growth control.

An additional plate with the same layout was also prepared but adding 4 μg/ml of potassium clavulanate (Fluka Ref 33454) to all plates in order to test the shift of the MIC in the presence of this β-lactamase inhibitor.

The inoculum was standardized to approximately $1 \times 10^7$ cfu/ml and diluted 1 in 200 in Middlebrook 7H9 broth complemented with ADC (Difco). This inoculum (200 μL and $10^4$ cfu/well) was added to the entire plate.

All plates were placed in a sealed box to prevent drying out of the peripheral wells and incubated at 37° C. without shaking for six days.

A Resazurin solution was prepared by dissolving one tablet of Resazurin (Resazurin Tablets for Milk Testing; Ref 330884Y VWR International Ltd) in 30 ml of sterile PBS (phosphate buffered saline). Of this solution, 25 μL were added to each well.

Fluorescence was measured (Spectramax M5 Molecular Devices, Excitation 530 nm, Emission 590 nm, cutoff 570 nm) after 48 hours to determine the MIC value Extracellular MIC values for sanfetrinem, including sanfetrinem cilexetil, and other representative β-lactams (meropenem, tebipenem, faropenem and ertapenem) are reported in Table 1 below. As can be seen, the raw data are reported along with an average MIC value. A difference of two times MIC value is considered within the margin of error. Each value reported, separated by a comma, is representative of a separate reading of MIC.

TABLE 1

| Compound | MIC μM (with clav) | MIC μM (w/o clav) | MIC μM (average with clav) | MIC μM (average w/o clav) |
|---|---|---|---|---|
| Sanfetrinem (sodium salt) | 1.25, 2.5, 5 | 2.5, 5, 7.5 | 2.9 | 5 |
| Sanfetrinem cilexetil | 5, 5, 10, 10, 5, 5, 20 | 10, 7.5, 10, 10, 7.5, 10, 10, 20 | 8.6 | 10.6 |
| Faropenem | 10, 5, 5, 5, 7.5, 20, 10 | 20, 10, 5, 5, 20, 30, 20 | 8.9 | 15.7 |
| Meropenem | 2.5, 5, 15, 5 | 15, 40, 40 | 6.9 | 31.7 |
| Tebipenem | 1.25 | 7.5 | 1.25 | 7.5 |
| Ertapenem | 10, 20, 20 | 80, >80, >80 | 16.7 | >80 |

Intracellular Viability Assay

The anti-tubercular activity of compounds against *Mycobacterium tuberculosis* growing inside human THP-1 monocytes was determined using *M. tuberculosis* H37Rv containing the Firefly luciferase gene.

THP-1 monocytes were maintained in suspension with RPMI-1640 media containing 10% FBS, 1 mM of Pyruvate, 2 mM of L-Glutamine, and incubated at 37° C. with 5% $CO_2$.

Monocytes were grown to sub-confluence ($5 \times 10^5$ cell/ml) and infected during 4 h in a cell roller bottle with a multiplicity of infection (MOI) of 1 with aseptic glass beads dispersed bacterial suspension in RPMI-0.05% Tween 80. Excess bacteria were removed by washing five times in RPMI media (1500 rpm 5 min.).

Infected cells were dispensed in 96 well white plates (50,000 cells/well) containing 1:2 serial dilutions of compounds. DMSO percentage must be below 0.5%.

Luminescence was measured after 5 days using the Steady-Glo Promega kit into a Victor 1420 system.

Results were processed by using Graf it software. MIC90 values are calculated from the dose-response curves by non-linear regression analysis.

Intracellular MIC50 values for sanfetrinem, including sanfetrinem cilexetil, and other representative β-lactams (meropenem, faropenem, tebipenem and ertapenem) are reported in Table 2 below. Intracellular MIC90 values for the same compounds are reported in Table 3. As can be seen, the raw data are reported along with an average MIC50 value and an average MIC90 value. A difference of two times MIC value is considered within the margin of error. Each value reported, separated by a comma, is representative of a separate reading of MIC.

TABLE 2

| Compound | MIC50 μM (with clav) | MIC50 μM (w/o clav) | MIC50 μM (average with clav) | MIC50 μM (average w/o clav) |
|---|---|---|---|---|
| Sanfetrinem (sodium salt) | 0.7, 2.06, 2.15 | 1.32, 1.64, 2 | 1.64 | 1.65 |
| Sanfetrinem cilexetil | 0.3, 0.9 | 0.49, 1.2 | 0.6 | 0.85 |
| Faropenem | 1.0, 1.2 | 2.2, 1.5 | 1.1 | 1.85 |
| Meropenem | 2.03, 1.85 | 8.97, 4.6 | 1.94 | 6.78 |
| Tebipenem | — | — | 0.49 | 4.51 |
| Ertapenem | — | — | 3.84 | 29.56 |

TABLE 3

| Compound | MIC90 μM (with clav) | MIC90 μM (w/o clav) | MIC90 μM (average with clav) | MIC90 μM (average w/o clav) |
|---|---|---|---|---|
| Sanfetrinem (sodium salt) | 6.13, 6.8, 8.82 | 2.13, 6.9, 7.69 | 7.25 | 5.57 |
| Sanfetrinem cilexetil | 4.6, 5.3 | 3.4, 7 | 5 | 5.2 |
| Faropenem | 6.8, 4.7 | 14.7, 10.0 | 5.75 | 12.35 |
| Meropenem | 5.39, 5.71 | 19.62, 14.41 | 5.55 | 17.01 |
| Tebipenem | — | — | 3.61 | 46.48 |
| Ertapenem | — | — | 21.02 | >50 |

In Vivo Experiment

To evaluate the in vivo anti-tubercular activity of sanfetrinem, an experimental design previously described in *Antimicrob Agents Chemother.* 2015 August; 59(8):4997-9 was used. However, a different background strain for the DHP-1 knockout mice was used: 129sv background instead of the C57Bl/6 background described in the paper.

In brief, specific pathogen-free, 8-10 week-old female 129sv DHP-1 KO mice were purchased and allowed to acclimate for one week. Mice were intratracheally infected with approximately 10e5 CFU/mouse (*M. tuberculosis* H37Rv). Compounds sanfetrinem sodium salt (SNF), sanfetrinem cilexetil (SNFc), meropenem (MRP), and clavulanate (CLV)) were administered twice a day from day 9 to day 14 after infection. MRP and SFN were administered subcutaneously. SFNc and CLV were administered by oral route. Lungs were harvested on days 9 or 15. All lung lobes were aseptically removed, homogenized and frozen. Homogenates were unfrozen and plated in 10% OADC-7H11 medium+0.4% activated charcoal for 18 days at 37° C.

Lung CFU count in untreated mice was 7.4 at Day 9 and 9.0 log CFU at Day 15. Lung CFU for subcutaneous (sc) SFN, oral (po) SFNc, and MRP-CLV treated mice were 7.3, 7.6, and 7.3 respectively (see FIG. 1). In FIG. 1, each dot represents data from one mouse. Mean lung CFU counts are shown over the dots for each group.

SFN and SFNc were equally efficacious versus MRP-CLV in this assay, with all three preventing bacterial growth.

Even though no net killing effect was observed, this experiment provides evidence that sanfetrinem and sanfetrinem cilexetil are both having an effect in vivo.

All animal studies were ethically reviewed and carried out in accordance with European Directive 2010/63/EU and the GSK Policy on the Care, Welfare and Treatment of Animals.

CONCLUSION

As evidenced by Tables 1-3, sanfetrinem possesses anti-mycobacterial activity, particularly against *Mycobacterium tuberculosis*, in both intracellular and extracellular assays. Sanfetrinem and sanfetrinem cilexetil also possess in vivo anti-tubercular activity.

In Vitro Activity of Sanfetrinem Against *M. tuberculosis* Clinical Isolates

Sanfetrinem (sodium salt) was tested against a panel of laboratory strains and clinical isolates, including both drug susceptible and drug resistant strains. Table 4 below provides a detailed description of the resistance patterns of the strains used.

TABLE 4

| Name | Background | Resistant profile |
|---|---|---|
| H37Rv | H37Rv | DS |
| dH37Rv H526D | H37Rv | RIF |
| clinical strain S531L | Clinical | RIF |
| 2A | Clinical | INH |
| 21 | Clinical | INH |
| 70 | Clinical | INH |
| 223 | Clinical | INH |
| 250 | Clinical | INH |
| 276 | Clinical | INH |
| 280 | Clinical | INH |
| 291 | Clinical | INH |
| 389R | Clinical | INH |
| Beijing 1137 | Clinical | DS |
| 52 S car1 | Clinical | DS |
| 215 car3 | Clinical | DS |
| 275 car5 | Clinical | DS |
| 2020 S car6 | Clinical | DS |
| 2166S car8 | Clinical | DS |
| Clinical Moxi R 488 | Clinical | MOX |
| Clinical Strep R | Clinical | STR |
| Line R | H37Rv | LZD |
| CDC 1551 | CDC1551 | DS |
| Erdman | Erdman | DS |

DS, drug susceptible; RIF, rifampicin; INH, isoniazid; MOX, moxifloxacin; STR, streptomycin; LZD, linezolid.

Bacterial Strains, General Growth Conditions and MGIT Susceptibility Assay

Strains were propagated at 37° C. in Middlebrook 7H9 broth (Difco) supplemented with 10% Middlebrook albumin-dextrose-catalase (ADC)(Difco), 0.2% glycerol and 0.05% (vol/vol). Susceptibility assays were performed using a MGIT 960 system from Becton Dickinson (BD) Medical Technology using BD BL MGIT tubes supplemented with BD BL MGIT OADC. Briefly, 7 mL MGIT tubes were added 0.8 mL OADC supplement, 0.1 mL of sanfetrinem DMSO stock solution and 0.1 mL of cells (final volume of MGIT tubes was 8 mL) to a final cell density of total $10^5$ cells per tube. This standard inoculum yielded a time-to-positivity (TTP) of 4 to 5 days. TTP was defined as the time needed for a bacterial culture to reach a MGIT Growth Index (GI) higher than 75. Sanfetrinem was assayed at four different concentrations, i.e, 0.5, 1.25, 5 and 20 µM. For every isolate, a stringent MIC cut-off was defined as the minimum concentration able to inhibit (GI<75) bacterial growth for at least 7 days. Rifampicin, isoniazid, moxifloxacin, linezolid and streptomycin were also used as internal controls of activity against clinical isolates.

Figure 2:
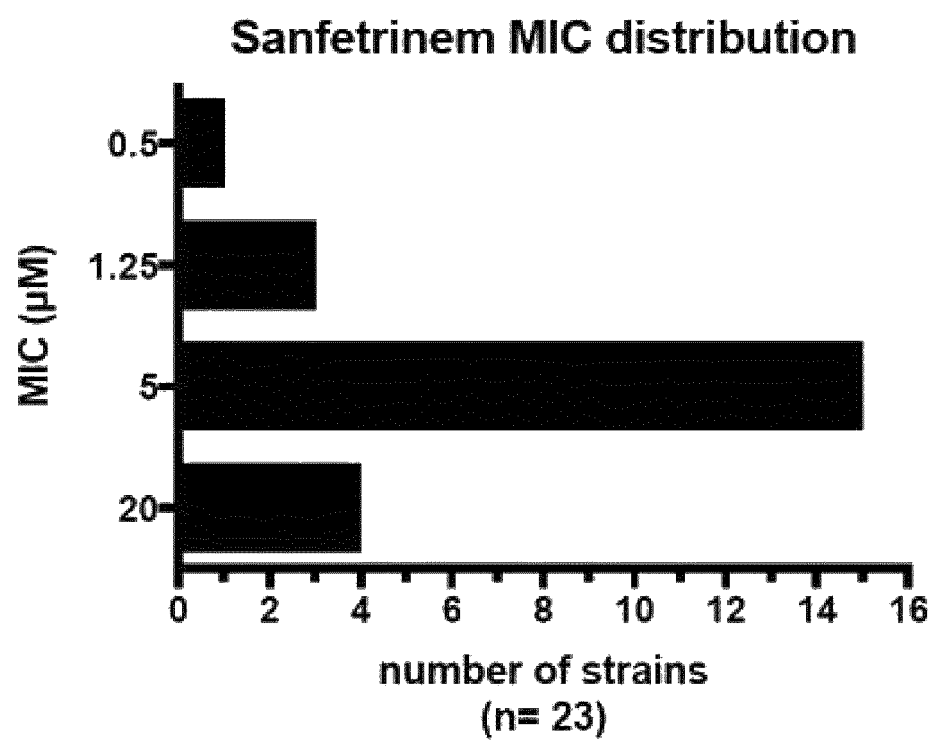
FIG. 2 is a plot of MIC distribution of sanfetrinem (sodium salt) against a panel of laboratory strains and clinical isolates.

The activity of sanfetrinem was tested against a panel of twenty-three *M. tuberculosis* strains, including clinical isolates with mono-resistant patterns of susceptibility. Four different concentrations of sanfetrinem were evaluated (0.5, 1.25, 5 and 20 µM). The number of strains sharing the same MIC values is displayed in FIG. 2. The most common MIC value was 5 µM (15 out of 23). Four strains displayed MIC values lower than 5 µM, while in the case of another four strains this value was higher. All strains were sensitive to sanfetrinem within the concentration range tested.

Combination Experiments

Further experiments were performed with sanfetrinem (sodium salt) in combination with other agents, such as amoxicillin (and clavulanic acid), rifampicin, ethambutol and delamanid.

Materials and Methods—Combination with Amoxicillin and/or Clavulanate

Checkerboard Plates

The experiment was performed in 96 well plates. Checkerboard plates of sanfetrinem (sodium salt) with amoxicillin were prepared. Amoxicillin was diluted along the abscissa from column 1 to 9 (from 80 µM to 0.3 µM) while sanfetrinem was diluted along the ordinate from row A to G (from 5 µM to 0.08 µM).

1:2 serial dilutions were used and the resulting checkerboard contained the combination of sanfetrinem and amoxicillin with the highest concentration of amoxicillin in column 1 and the highest concentration of sanfetrinem in row A.

In order to confirm their individual MICs, column 10 contained sanfetrinem alone and row H contained amoxicillin alone.

Inoculum with DMSO as the positive growth control was dispensed from A12 to D12, and inoculum plus rifampicin (R3501_Sigma) at 1 µg/ml as inhibition control was dispensed from E12 to H12. With these controls, it was possible to establish Z' values and the signal to background as quality control of the plates in the assay.

In column 11, moxifloxacin was dispensed as control of the assay from A11 (1 µg/ml) to H11 (0.008 µg/ml) to provide a dose response curve.

Four identical plates were generated, and in two of these potassium clavulanate (33454-100MG SIGMA) was added to the checkerboard at a concentration of 4 µg/ml. The experiment was run with and without clavulanate.

A second set of four plates with the same design but with less amoxicillin concentration (5 µM to 0.02 µM in Columns 1 to 9) was also prepared to ensure that all relevant drug concentrations were being explored.

Inoculum

The media used was 7H9-ADC-Tyloxapol. 4.7 g Middlebrook 7H9 broth base was dissolved in 900 mL deionized water. 5 mL of 10% w/v Tyloxapol and 10% Albumin- Dextrose-Catalase (ADC) enrichment (Becton Dickinson) was then added. The strain used was *M. tuberculosis* H37Rv and when the culture was in the exponential phase of the growth, the culture was standardised to approximately $1 \times 10^7$ CFU/mL (OD600=0.125). The culture was then diluted 1:200 in 7H9-ADC-Tyloxapol and 200 µL of this inoculum added to each well at $5 \times 10^4$ CFUs/ml. The plates were incubated at 37° C. for 6 days.

Readout

Resazurin was used as readout. One resazurin tablet (Ref R/0040/79_Fisher Scientific) was dissolved in 30 ml PBS. This solution was sterilized by filtration (0.22 µm). 25 µl of the sterilized solution was added into each well and the plates incubated for 48 additional hours at 37° C. After incubation fluorescence at SpectraMax M5 (Molecular Devices) was determined. The settings were: Excitation 530 nm; Emission 590 nm (cutoff 570 nm).

Data Analysis

Every assay plate contained a set of negative controls with DMSO, which corresponded to 100% bacterial growth, and a set of positive controls (1 µg/ml of rifampicin) in which 100% inhibition of bacterial growth is reached. These controls were used to monitor assay quality through determination of Z' as well as for normalizing the data (Growth %) on a per-plate basis.

Each set of dose-response measurements of sanfetrinem (Growth % vs. [sanf]) for the different cases: in monotherapy and in combination with amoxicillin (at different concentrations) and/or clavulanic; was fitted to the following Hill type equation with four parameters (Top, Bottom, XC50 and HillSlope):

Growth %=Bottom+(Top−Bottom)/(1+10^((Log XC50−Log[sanf])*HillSlope))

The nonlinear regression curve fitting method available in the software GraphPad Prism 6 was used to compute the parameters for each case.

Note that in this equation XC50 represents the concentration to reach the value of Growth % half way between Bottom and Top. The parameter of interest is the concentration of sanfetrinem to reach a 90% Inhibition (i.e. a 10% Growth), denoted herein by IC90. Using the equation above, this parameter can be computed directly from the estimated parameters as follows:

IC90=XC50*((10%−Bottom)/(Top−10%))^(1/HillSlope)

For the characterisation of amoxicillin in monotherapy, since it does not reach a 90% Inhibition, the IC80 was computed instead. This parameter was computed analogously from the estimated parameters resulting from the non-linear fitting of the corresponding dose-response measurements: Growth % vs. [amox].

Results

Figure 3:
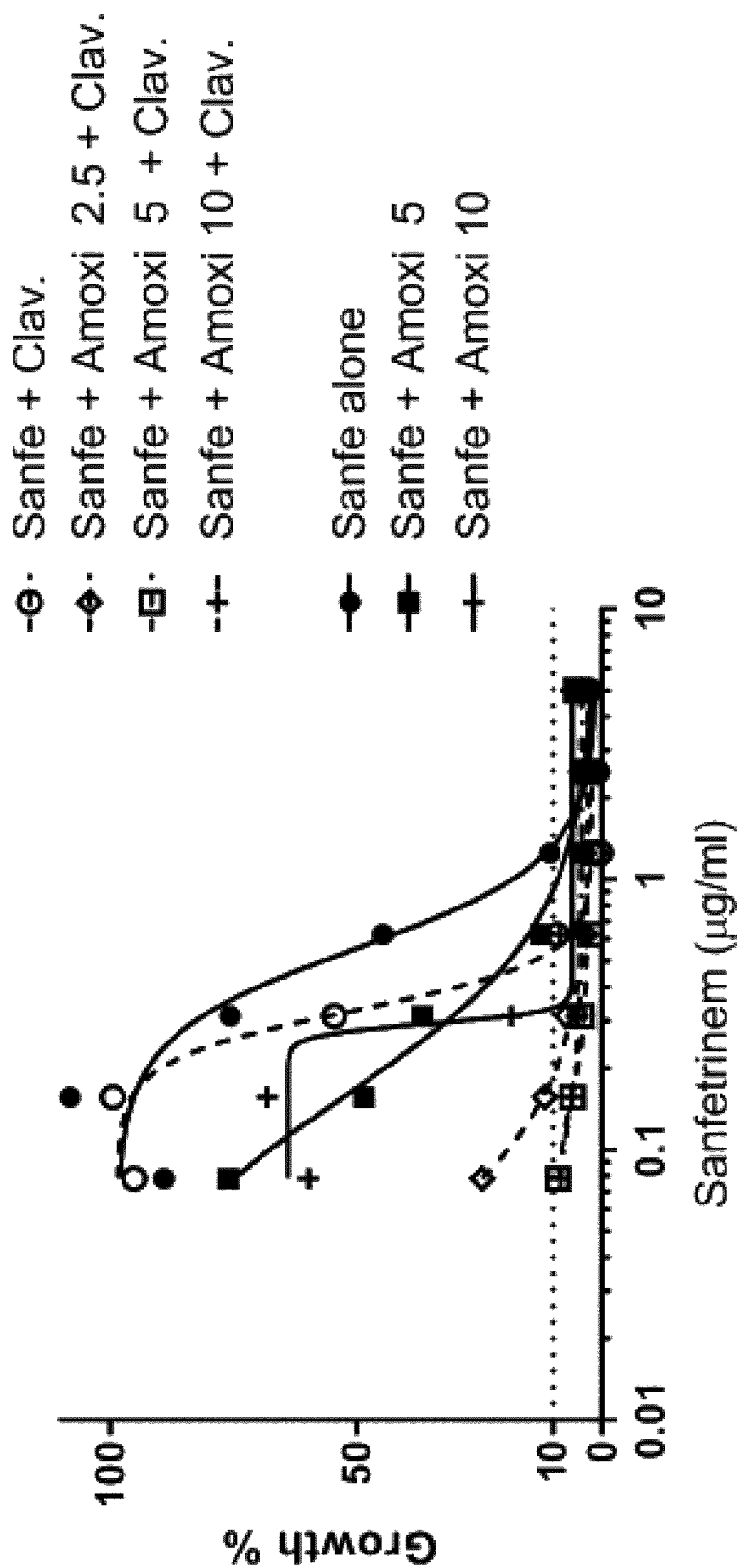
FIG. 3 shows dose-response curves of sanfetrinem, % Growth versus concentration, alone and in combination with amoxicillin and with amoxicillin plus clavulanate (concentration values of amoxicillin are in μg/mL).
Figure 4:
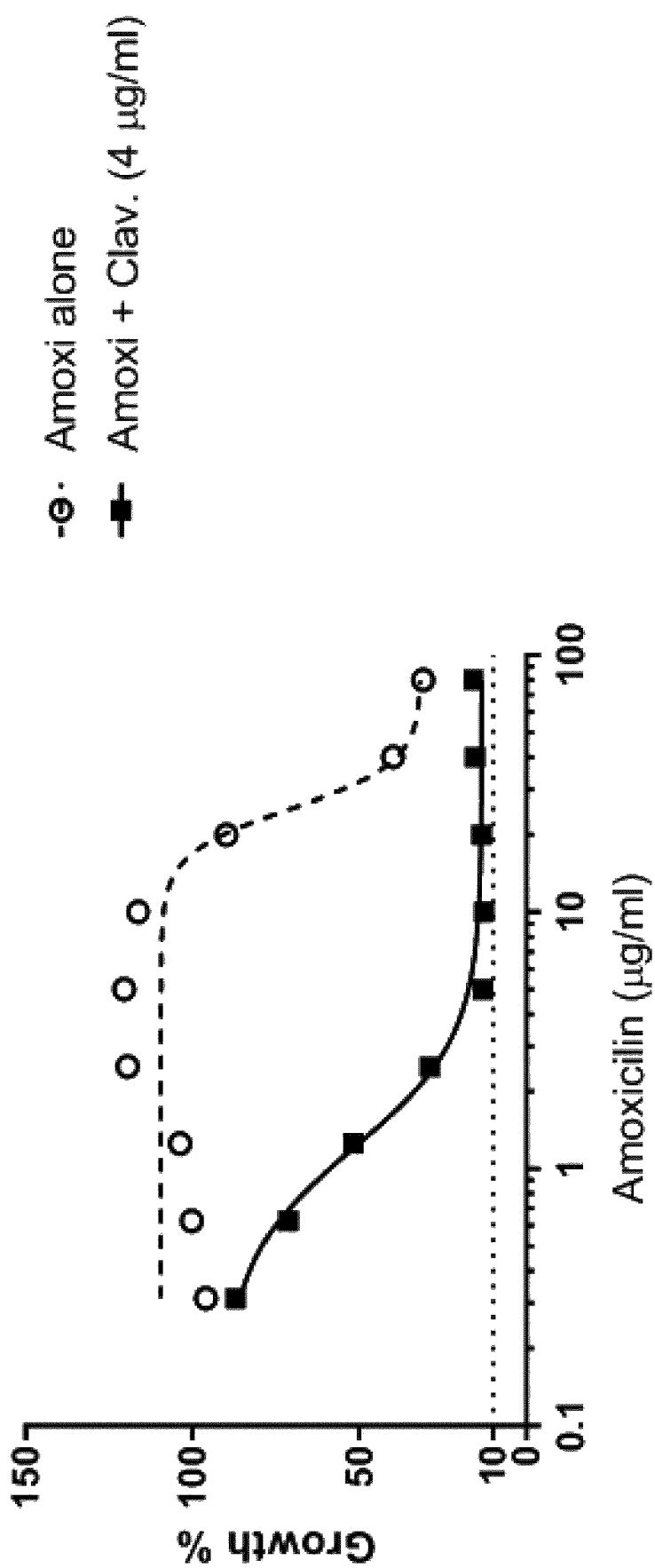
FIG. 4 shows dose-response curves of amoxicillin, % Growth versus concentration, alone and in combination with clavulanate.
Figure 5:
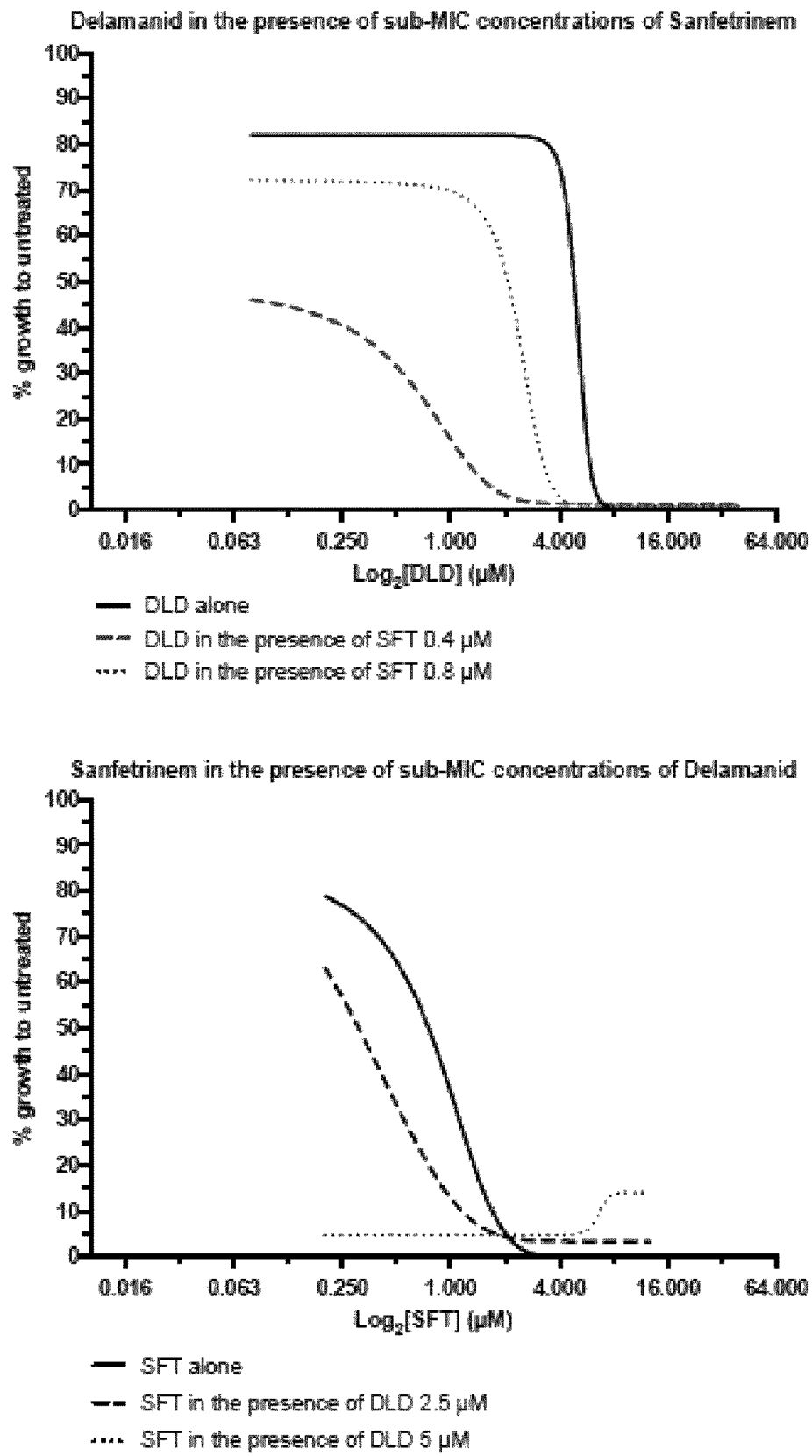
FIG. 5 shows dose-response curves for sanfetrinem alone and in combination with delamanid.
Figure 6:
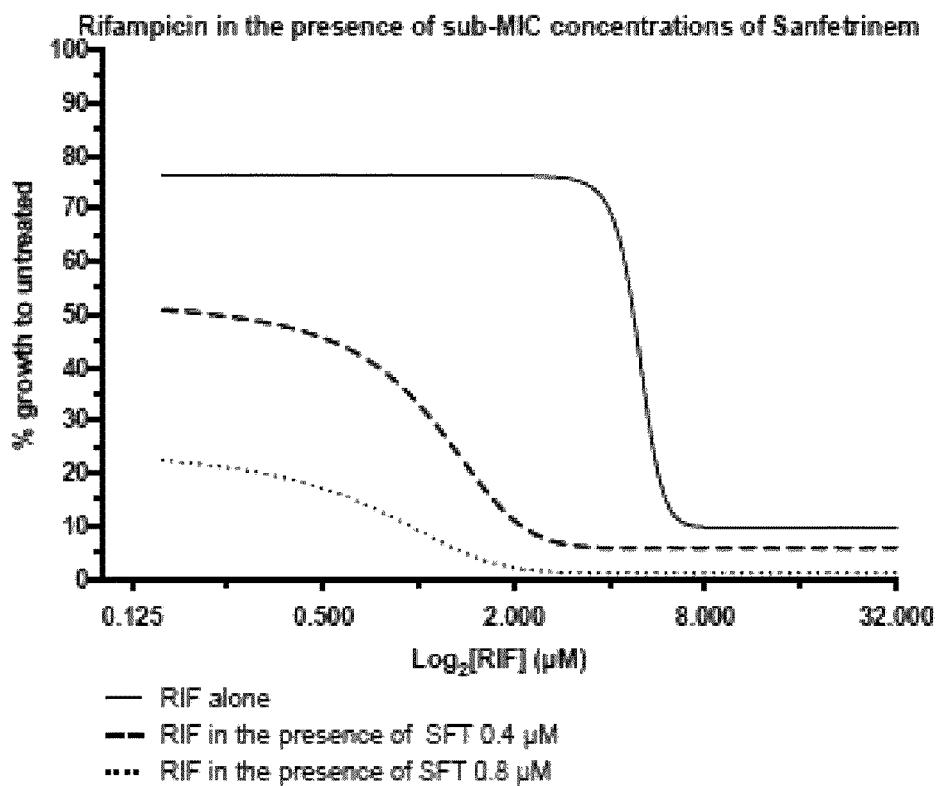
FIG. 6 shows dose-response curves for sanfetrinem alone and in combination with rifampicin.
Figure 6:
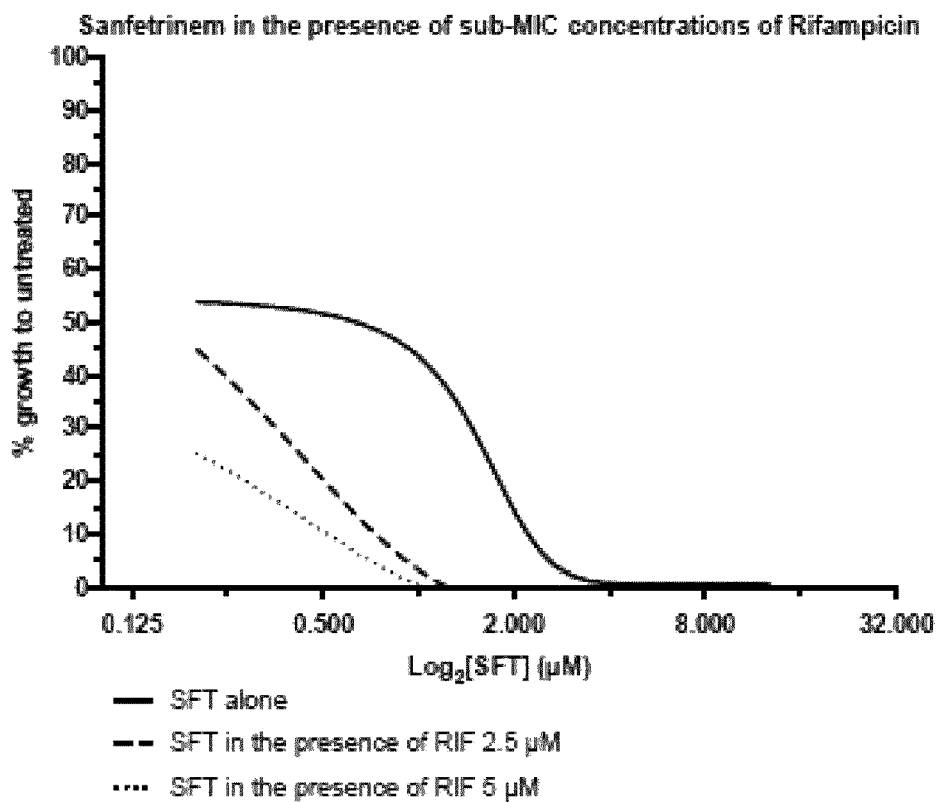

The data are reported in Table 5 and FIGS. 3 and 4.

TABLE 5

| Compounds | IC90 (µg/ml) |
|---|---|
| Sanfetrinem | 1.22 |
| Sanfetrinem + Clav | 0.55 |
| Sanfetrinem + Amoxicillin (5 µg/ml) | 0.91 |
| Sanfetrinem + Amoxicillin (5 µg/ml) + Clav | 0.1 |
| Sanfetrinem + Amoxicillin (10 µg/ml) | 0.33 |
| Sanfetrinem + Amoxicillin (10 µg/ml) + Clav | 0.1 |

It should be noted that amoxicillin was tested alone and an IC80 (in µg/mL) value of 42 was observed. Amoxicillin and potassium clavulanate were also tested in combination and an IC80 (in µg/mL) value of 3.9 was observed.

The Fractional Inhibitory Concentration Index (FICI) (Synergy, antagonism, and what the chequerboard puts between them. Odds, F.C. 1, s.I., *Journal of Antimicrobial Chemotherapy*, 2003, Vol. 52), which is based on the Loewe additivity model (What is synergy? The Saariselkä agreement revisited. Tang J., Wennerberg K. and Aittokallio T. 181, s.I., *Frontiers in Pharmacology*, 2015, Vol. 6), for the 90% growth inhibition (denoted by $FICI_{90}$) is considered herein for the assessment of the synergy of combinations in this extracellular activity in-vitro assay. An FICI of 0.5 is considered to represent synergy. This characterisation/quantification of synergy is exploratory and does not explain actual synergy or antagonism mechanism (as noted by Tang J., Wennerberg K. and Aittokallio T.).

Figure 7:
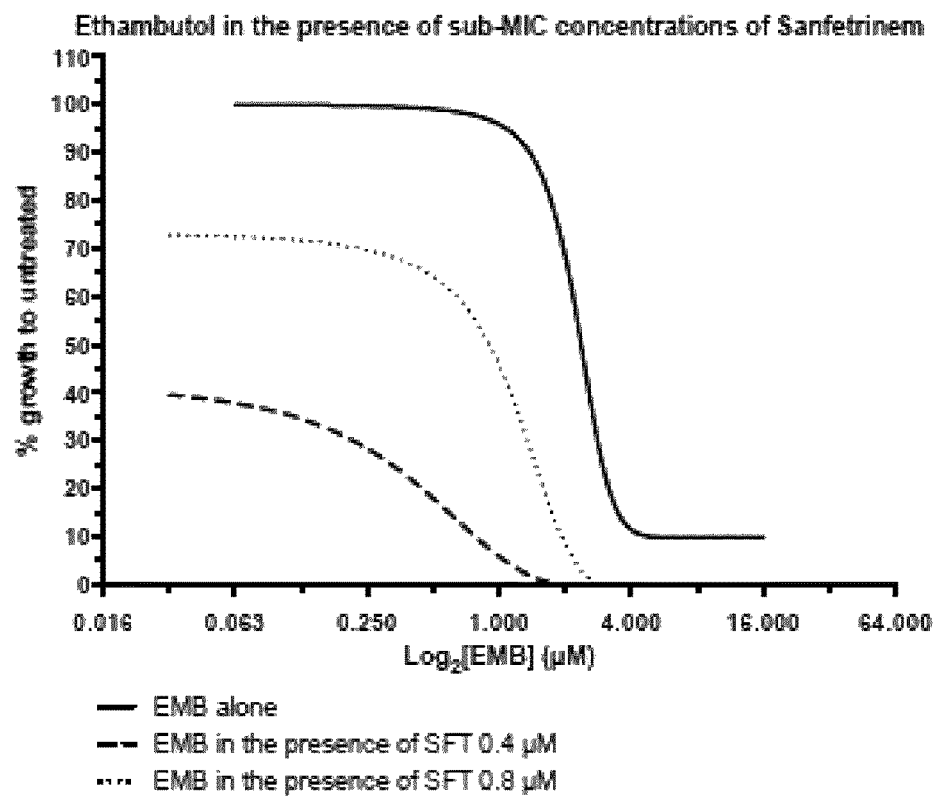
FIG. 7 shows dose-response curves for sanfetrinem alone and in combination with ethambutol.
Figure 7:
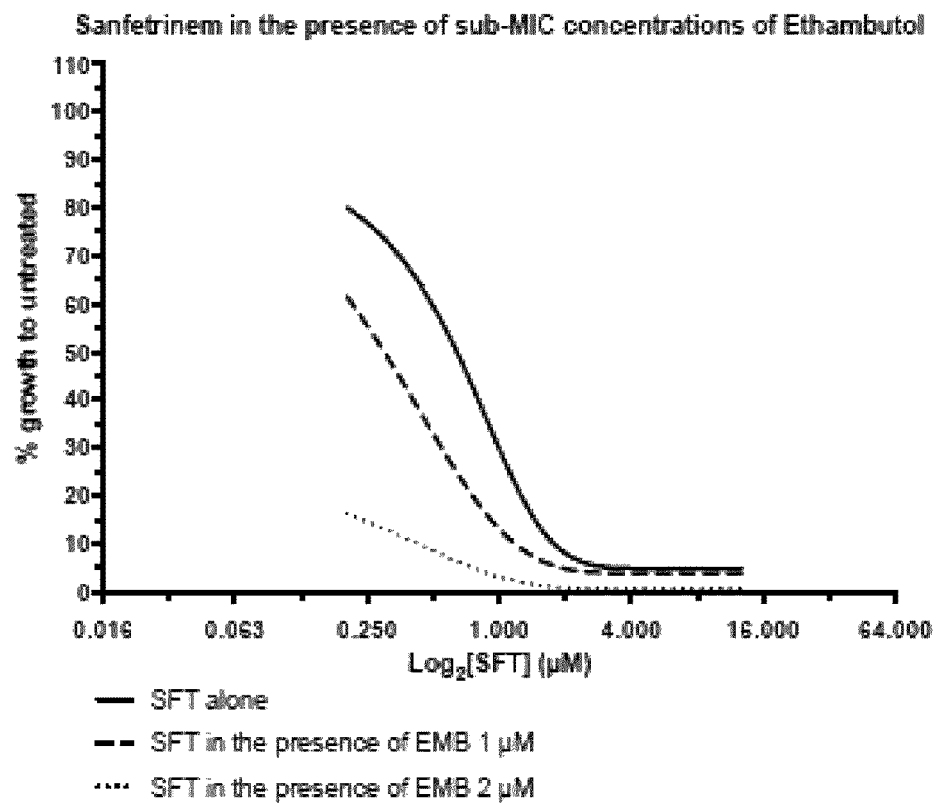
Figure 8:
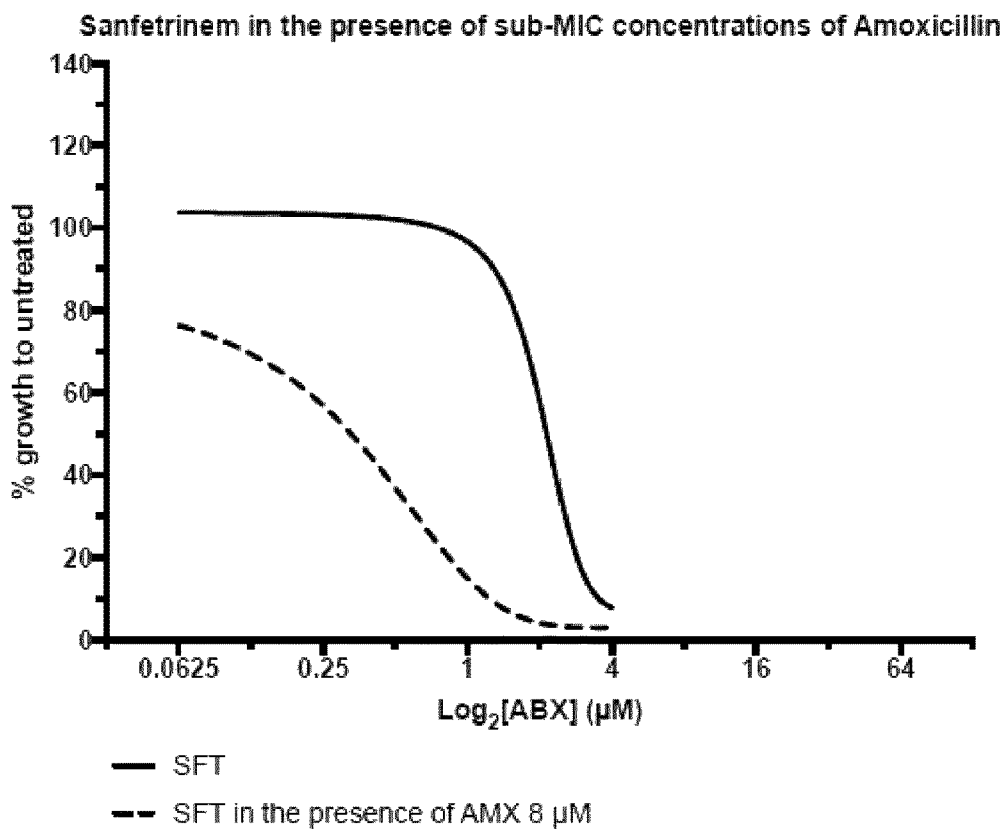
FIG. 8 shows dose-response curves for sanfetrinem alone and in combination with amoxicillin.
Figure 8:
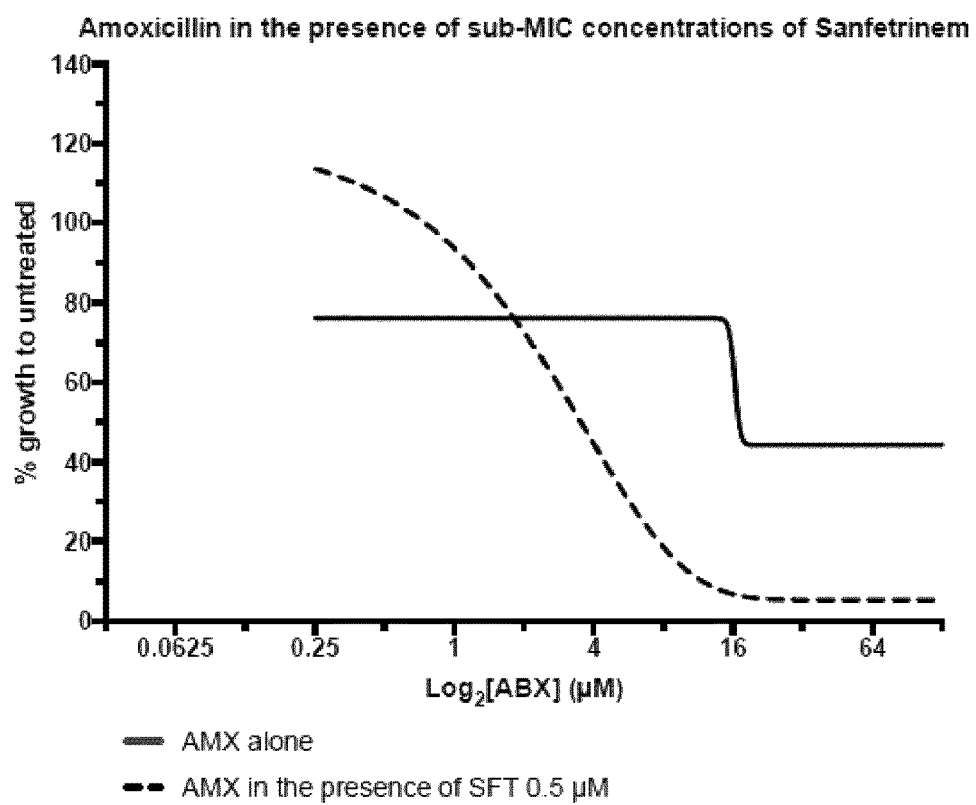

The $FICI_{90}$ calculation entails the IC90s of sanfetrinem alone, 1.22 µg/ml; in combination with clavulanate, 0.55 µg/ml; in combination with amoxicillin (at 10 µg/ml), 0.33 µg/ml; and in combination with amoxicillin (at 5 µg/ml)+clavulanate, 0.1 µg/ml. Since clavulanate alone is not active and neither amoxicillin alone nor in combination with clavulanate reach the 90% growth inhibition (FIG. 7: Dose-response Amoxicillin), the corresponding fractional terms in the computation of the $FIC_{90}$ are zero:

Sanfetrinem+Clavulanate:

$FICI_{90}=0.55/1.22=0.45$

This is almost one dilution, so it is not considered that this represents significant synergy.

Sanfetrinem+Amoxicilin (10 µg/ml):

$FICI_{90}=0.33/1.22=0.27$

This combination is considered to represent synergy.

Sanfetrinem+Amoxicilin (5 µg/ml)+Clavulanate:

$FICI_{90}=0.1/1.22=0.1$

This combination is considered to represent synergy.

Materials and Methods—Combinations of Sanfetrinem (Sodium Salt) with Rifampicin (RIF), Ethambutol (EMB), Delamanid (DLD) and Amoxicillin (AMX)

Bacterial Strain and General Growth Conditions

The Mtb H37Rv strain was routinely propagated at 37° C. in Middlebrook 7H9 broth (Difco) supplemented with 10% Middlebrook albumin-dextrose-catalase (ADC)(Difco), 0.2% glycerol and 0.05% (vol/vol).

Drug Susceptibility Assay

Stock solutions of compounds used in this study were always prepared fresh on the same day of plate inoculation. For use in a 384-well plate format, compounds were dissolved in DMSO and dispensed using an HP D3000 Digital Dispenser and HP T8 Dispenserhead Cassettes (Ref No. CV081A) in two-fold dilutions.

Minimal Inhibitory Concentrations (MIC) were determined in 7H9-based broth medium. This was supplemented with 0.2% glycerol and 10% ADC without tyloxapol. Mycobacterial cells were grown to an $OD_{600}$=0.5-0.8 and stocks were frozen at −80° C. Upon thawing, cells were diluted in assay medium to a final concentration of $10^5$ cells/mL and dispensed in the plates 50 uL/well. MTT [3-(4,5-dimethyl-thiazol-2-yl)-2,5-diphenyl tetrazolium bromide] (Stock 5 mg/mL Acros Organics ref 15224654) and the Bactiter-Glo Luciferase Assay System (Promega, Madison, Wis.) were used as cell growth indicators for the Mtb H37Rv strain. Luminescence was measured in an Envision Multilabel Plate Reader (PerkinElmer) using a white opaque 384-plate (781075_Greiner) Ultra Sensitive luminescence mode, with a measurement time of 50 ms per well for the Bactiter-Glo system and OD 580 nm was measured in a Spectramax M5 (Molecular Devices) reader using the black 384-microclear plate (781091_Greiner) for the MTT read-out.

Plates were incubated for 7 days before measurement of ATP production (according to manufacturer indications) or MTT to formazan conversion (25 uL/well from stock at day 6 and 25 uL/well of 10% SDS at day 7), respectively. The lowest concentration of drug that inhibited 90% of MTT conversion or ATP production compared to internal control wells with no drug added (DMSO control) was used to define MIC values (IC90).

Checkerboard Assay

Drug activity was determined in 384-well plate format using the MTT or ATP assay, as described above. The fractional inhibitory concentration (FIC) for each compound was calculated as follows: FICA=(MIC of compound A in the presence of compound B)/(MIC of compound A alone). Similarly, the FIC for compound B was calculated. The FIC Index (FICI) was calculated as: FICI=[FICA+FICB]. An FICI of 0.5 is considered to represent synergy Checkerboard plates of sanfetrinem (sodium salt) with rifampicin were prepared. Rifampicin was diluted along the abscissa from column 12 to 3 (from 0.08 µM to 0.00015625 µM) while sanfetrinem was diluted along the ordinate from row A to G (from 12.8 µM to 0.4 µM).

Column 2 and row H were used to calculate individual MICs (sanfetrinem and rifampicin respectively). Equivalent positions in quadrant 2, 3 and 4 were used for ethambutol and delamanid and amoxicillin.

Delamanid was diluted from 40 nM to 0.078 nM and ethambutol was diluted from 32 µM to 0.06 µM. Amoxicillin was diluted from 128 µM to 0.25 µM. Each of them were dispensed in equivalent positions in quadrant 2 and 3 respectively.

Results

The data are reported in Table 6 and FIGS. 5 to 8. All MIC values in Table 6 are reported in µM.

TABLE 6

| Comp A | Comp B | MIC of A | MIC of B | MICsyn_A | MICsyn_B | Fold_A | Fold_B | FIC_A | FIC_B | FICI |
|---|---|---|---|---|---|---|---|---|---|---|
| SFT | RIF | 3.2 | 0.04 | 0.4 | 0.005 | 8 | 8 | 0.125 | 0.125 | 0.25 |
| SFT | EMB | 1.6 | 8 | 0.4 | 2 | 4 | 4 | 0.25 | 0.25 | 0.5 |
| SFT | DLD | 1.6 | 0.01 | 0.4 | 0.0025 | 4 | 4 | 0.25 | 0.25 | 0.5 |
| SFT | AMX | 4 | 128 | 0.5 | 8 | 8 | 16 | 0.125 | 0.0625 | 0.1875 |

The following terminology has been used in Table 6.
Comp Compound
MIC Minimum Inhibitory Concentation in µM
MICsyn Synergistic MIC of the compound tested (either A or B) in the presence of the other compound (either B or A, respectively)
Fold MIC/MICsyn
FIC Fractional Inhibitory Concentration. MIC of A or B in the presence of B or A, respectively/MIC A or B alone
FICI Fractional Inhibitory Concentration Index. FIC_A+FIC_B. A value of 0.5 is believed to be indicative of a synergistic interaction

The invention claimed is:

1. A method for the treatment of a disease resulting from a mycobacterial infection in a human in need thereof, comprising administering to said human a therapeutically effective amount of a compound which is

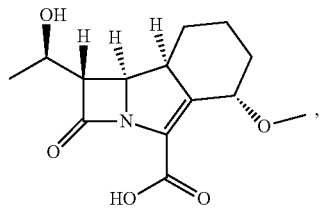 [SMILES: CO[C@H]1CCC[C@H]2C1=C(C(=O)O)N1C(=O)[C@H]([C@@H](C)O)[C@@H]21]

or a pharmaceutically acceptable salt thereof.

2. The method according to claim 1, wherein the disease is tuberculosis.

3. A method for the treatment of a disease resulting from a mycobacterial infection in a human in need thereof, comprising administering to said human a therapeutically effective amount of a compound which is

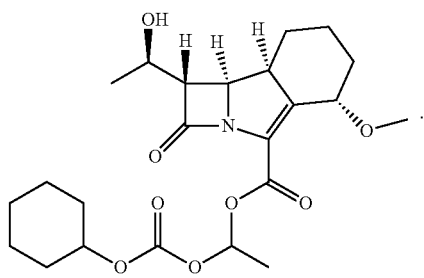 [SMILES: CO[C@H]1CCC[C@H]2C1=C(C(=O)OC(C)OC(=O)OC1CCCCC1)N1C(=O)[C@H]([C@@H](C)O)[C@@H]21]

or a pharmaceutically acceptable salt thereof.

4. The method according to claim 1, wherein the compound or salt thereof is a sodium salt of compound which is

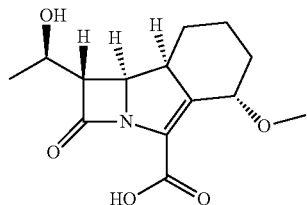 [SMILES: CO[C@H]1CCC[C@H]2C1=C(C(=O)O)N1C(=O)[C@H]([C@@H](C)O)[C@@H]21]

5. A method of treating tuberculosis in a human in need thereof, comprising administering to said human a composition comprising (a) the compound which is

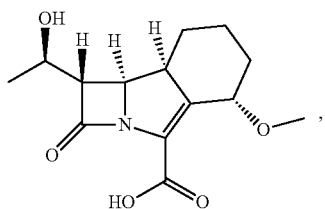 [SMILES: CO[C@H]1CCC[C@H]2C1=C(C(=O)O)N1C(=O)[C@H]([C@@H](C)O)[C@@H]21]

or a pharmaceutically acceptable salt or ester prodrug thereof, wherein the ester prodrug is

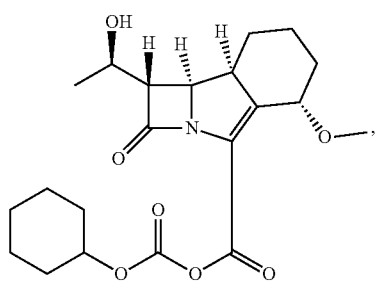 [SMILES: CO[C@H]1CCC[C@H]2C1=C(C(=O)OC(=O)OC1CCCCC1)N1C(=O)[C@H]([C@@H](C)O)[C@@H]21]

or a pharmaceutically acceptable salt thereof, and
(b) a pharmaceutically acceptable excipient.

6. A method of treating tuberculosis in a human in need thereof, comprising administering to said human a combination comprising
(a) the compound which is

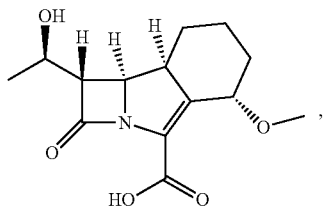 [SMILES: CO[C@H]1CCC[C@H]2C1=C(C(=O)O)N1C(=O)[C@H]([C@@H](C)O)[C@@H]21]

or a pharmaceutically acceptable salt or ester prodrug thereof, wherein the ester prodrug is

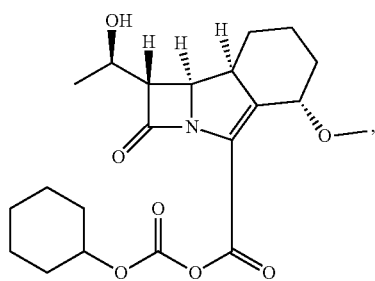 [SMILES: CO[C@H]1CCC[C@H]2C1=C(C(=O)OC(=O)OC1CCCCC1)N1C(=O)[C@H]([C@@H](C)O)[C@@H]21]

or a pharmaceutically acceptable salt thereof, and
(b) a further anti-tuberculosis agent.

7. The method according to claim 6, wherein the further anti-tuberculosis agent is selected from isoniazid, rifampin, pyrazinamide, ethambutol, moxifloxacin, rifapentine, clofazimine, ethionamide, prothionamide, isoxyl, thiacetazone, rifabutin, a diarylquinoline such as bedaquiline (TMC207) or TBAJ-587, nitroimidazo-oxazine PA-824, delamanid (OPC-67683), an oxazolidinone, linezolid, tedizolid, radezolid, sutezolid (PNU-100480), posizolid (AZD-5847), TBI-223, EMB analogue SQ109, OPC-167832, GSK3036656 (GSK070), GSK2556286, GSK3211830, a benzothiazinone, BTZ043, PBTZ169, an azaindole, TBA-7371, a dinitrobenzamide, a beta-lactam, meropenem, faropenem, ertapenem, tebipenem, beta-lactam combinations, and AUGMENTIN (amoxicillin-clavulanate).

8. The method according to claim 6, wherein the further anti-tuberculosis agent is AUGMENTIN (amoxicillin-clavulanate).

9. The method according to claim 6, further comprising an antiretroviral agent.

10. The method according to claim 9, wherein the antiretroviral agent is selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068, BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

11. A method for the treatment of a disease resulting from a mycobacterial infection in a human in need thereof, comprising administering to said human (a) the compound

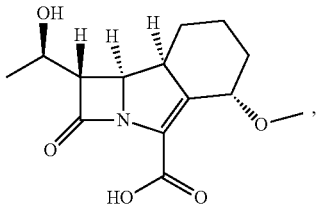 [SMILES: CO[C@H]1CCC[C@H]2C1=C(C(=O)O)N1C(=O)[C@H]([C@@H](C)O)[C@@H]21]

or a pharmaceutically acceptable salt or ester prodrug thereof; wherein the ester prodrug is

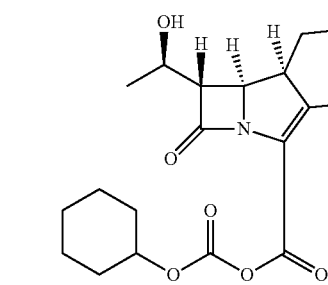

or a pharmaceutically acceptable salt thereof, and
(b) a β-lactamase inhibitor.

12. The method of claim 11 wherein the disease is tuberculosis.

13. The method of claim 11 wherein the β-lactamase inhibitor is clavulanate or clavulanic acid.

14. The method according to claim 3, wherein the disease is tuberculosis.

* * * * *